(12) United States Patent
Sinderby et al.

(10) Patent No.: US 9,308,338 B2
(45) Date of Patent: Apr. 12, 2016

(54) DETECTION OF DYNAMIC HYPERINFLATION IN SPONTANEOUSLY BREATHING MECHANICALLY VENTILATED PATIENTS

(75) Inventors: Christer Sinderby, Toronto (CA); Jennifer Beck, Toronto (CA); Norman Comtois, Scarborough (CA); Giacomo Grasselli, Milan (IT)

(73) Assignee: ST. MICHAEL'S HOSPITAL, Toronto, Ontario (CA)

( * ) Notice: Subject to any disclaimer, the term of this patent is extended or adjusted under 35 U.S.C. 154(b) by 1278 days.

(21) Appl. No.: 13/143,666

(22) PCT Filed: Jan. 7, 2010

(86) PCT No.: PCT/CA2010/000017
§ 371 (c)(1),
(2), (4) Date: Sep. 21, 2011

(87) PCT Pub. No.: WO2010/081214
PCT Pub. Date: Jul. 22, 2010

(65) Prior Publication Data
US 2012/0118290 A1 May 17, 2012

Related U.S. Application Data

(60) Provisional application No. 61/193,974, filed on Jan. 14, 2009.

(51) Int. Cl.
*A61M 16/00* (2006.01)
*A61B 5/091* (2006.01)

(52) U.S. Cl.
CPC ............ *A61M 16/0051* (2013.01); *A61B 5/091* (2013.01); *A61M 16/0003* (2014.02); *A61M 2016/003* (2013.01); *A61M 2016/0036* (2013.01)

(58) Field of Classification Search
CPC ............ A61M 16/00; A61M 16/0003; A61M 16/0051; A61M 2016/0027; A61M 2016/003; A61M 2016/0033; A61M 2016/0036
See application file for complete search history.

(56) References Cited

U.S. PATENT DOCUMENTS

| 4,693,256 A | 9/1987 | Talonn |
| 5,456,264 A * | 10/1995 | Series et al. ............. 600/538 |

(Continued)

FOREIGN PATENT DOCUMENTS

| WO | 97/22377 | 6/1997 |
| WO | 2006/012205 | 2/2006 |
| WO | 2006/127573 | 11/2006 |

OTHER PUBLICATIONS

Blanch et al. "Measurement of Air Trapping, Intrinsic Positive End-in Expiratory Pressure, and Dynamic Hyperinflation in Mechanically Ventilated Patients", *Respiratory Care*, Jan. 2005, vol. 50, No. 1, pp. 110-124.

*Primary Examiner* — Justine Yu
*Assistant Examiner* — Colin W Stuart
(74) *Attorney, Agent, or Firm* — Fay Kaplun & Marcin, LLP

(57) ABSTRACT

A method and device for determining dynamic hyperinflation during mechanical ventilation of a spontaneously breathing patient, wherein mechanical ventilation is removed during one breath of the patient, inspiratory and expiratory volumes of the patient are measured during the one breath, and a difference between the inspiratory and expiratory volumes measured during the one breath is calculated. Dynamic hyperinflation of the patient's lungs is indicated in relation to the calculated difference.

19 Claims, 5 Drawing Sheets

(56) References Cited

U.S. PATENT DOCUMENTS

| | | |
|---|---|---|
| 2003/0226565 A1 | 12/2003 | Sinderby et al. |
| 2005/0211246 A1 | 9/2005 | Beck et al. |
| 2005/0284476 A1* | 12/2005 | Blanch et al. ............ 128/204.21 |
| 2006/0206036 A1 | 9/2006 | Quinn |
| 2007/0049843 A1* | 3/2007 | Derchak ....................... 600/538 |
| 2007/0142742 A1 | 6/2007 | Aljuri et al. |

* cited by examiner

DETECTION OF DYNAMIC HYPERINFLATION IN SPONTANEOUSLY BREATHING MECHANICALLY VENTILATED PATIENTS

FIELD

The present invention relates to a method and device for determining dynamic hyperinflation during mechanical ventilation of a spontaneously breathing patient.

BACKGROUND

Intrinsic positive end-expiratory pressure (intrinsic PEEP or PEEPi) is a phenomena occurring due to insufficient expiratory time, preventing the lungs of a patient from becoming sufficiently emptied at the end of expiration, trapping air in the lungs, and increasing the end-expiratory lung volume (dynamic hyperinflation).

During mechanical ventilation of a patient, the presence of dynamic hyperinflation and intrinsic PEEP (PEEPi) can be aggravated by high levels of mechanical ventilation and trigger/off-cycling settings on the mechanical ventilator.

Clinical methods to detect/quantify intrinsic PEEP (PEEPi) comprise measuring pressures at an opening of mechanically ventilating airways during occlusions of those airways; such methods are difficult to interpret during spontaneous breathing.

SUMMARY

According to a first aspect of the invention, there is provided a method for determining dynamic hyperinflation during mechanical ventilation of a spontaneously breathing patient, comprising: removing mechanical ventilation during one breath of the patient; measuring inspiratory and expiratory volumes of the patient during said one breath; calculating a difference between the inspiratory and expiratory volumes measured during said one breath; and indicating dynamic hyperinflation of the patient's lungs in relation to the calculated difference.

According to a second aspect of the invention, there is provided a device for determining dynamic hyperinflation during mechanical ventilation of a spontaneously breathing patient, comprising: a controller for removing mechanical ventilation during one breath of the patient; a sensor of inspiratory and expiratory volumes of the patient during said one breath; a calculator of a difference between the inspiratory and expiratory volumes sensed during said one breath; and an indicator of dynamic hyperinflation of the patient's lungs in relation to the calculated difference.

BRIEF DESCRIPTION OF THE DRAWINGS

The foregoing and other features of the present invention will become apparent from reading of the following non restrictive description of an illustrative embodiment thereof, given by way of example only with reference to the accompanying drawings in which.

DETAILED DESCRIPTION

As described hereinabove, the concept of air-trapping relates to a quantity of air penetrating the lungs of a patient larger than the quantity of air leaving the patient's lungs. Air-trapping induced by mechanical ventilation actually worsens contractility of the inspiratory muscles due to dynamic hyperinflation until a level where weakness of the inspiratory muscles and added mechanical ventilation reach an equilibrium causing inspiratory (Vins) and expiratory (Vexp) volumes to match.

When mechanical ventilation is removed in the presence of air-trapping, the patient has difficulty to inhale due to lost mechanical ventilation and weak inspiratory muscles. However, due to extra stored energy i.e. increased elastic recoil in the inspiratory muscles due to air-trapping, the patient has no difficulty to generate force to exhale.

Accordingly, air-trapping during mechanical ventilation should hence result in similar inspiratory (Vins) and expiratory (Vexp) volumes during breaths with mechanical ventilation, whereas inspiratory volumes (Vins) are smaller than expiratory volumes (Vexp) during the first breaths after mechanical ventilation has been removed. When the lungs are not trapping air, the inspiratory (Vins) and expiratory (Vexp) volumes should be similar for breaths both with mechanical ventilation and without mechanical ventilation. With these concepts in mind, FIG. 1 of the appended drawings illustrates a device 100 for determining dynamic hyperinflation during mechanical ventilation of a spontaneously breathing patient.

Figure 1:
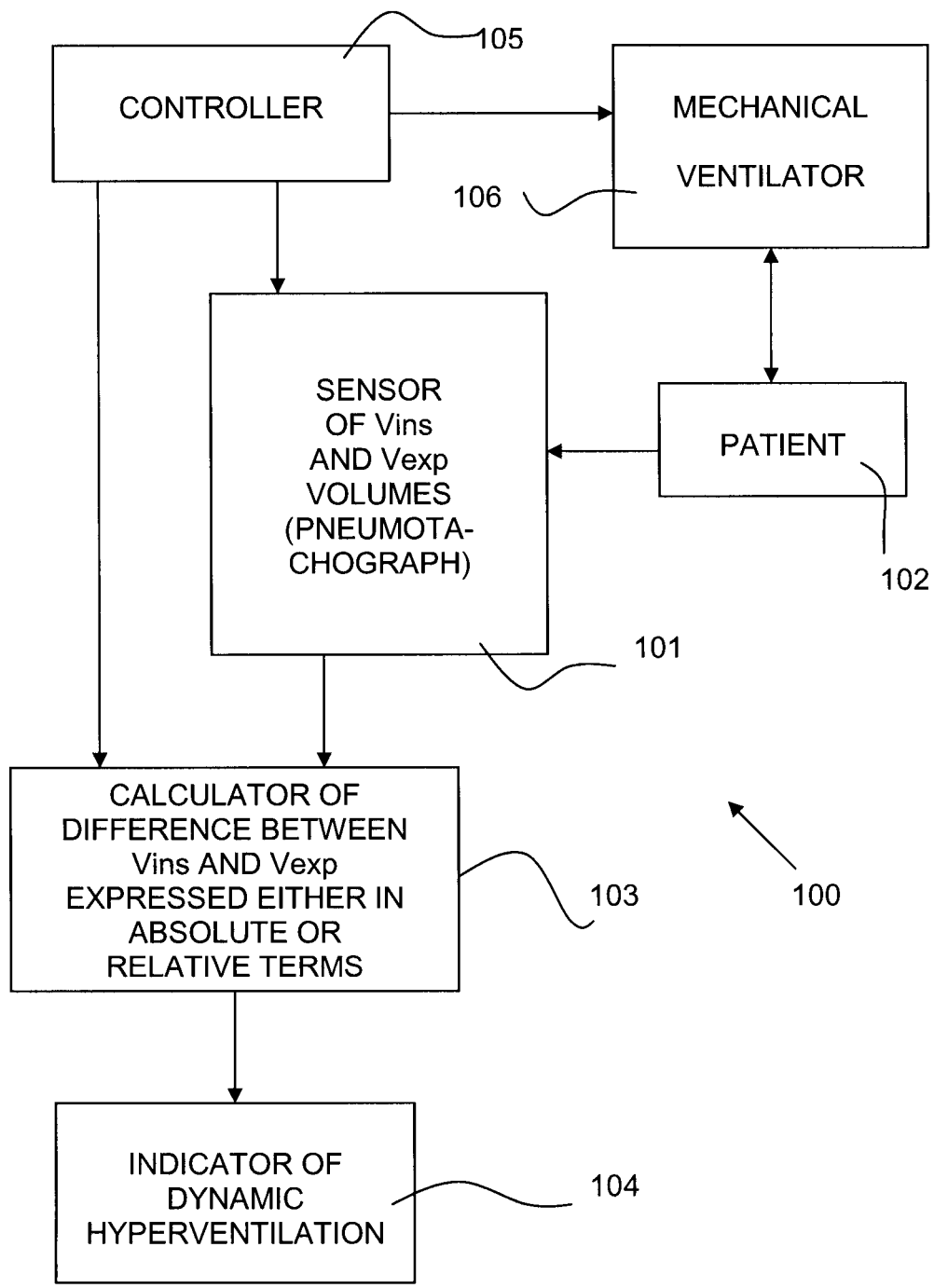
FIG. 1 is a schematic block diagram of a device for determining dynamic hyperinflation during mechanical ventilation of a patient.

The device 100 of FIG. 1 comprises a sensor 101 of inspiratory (Vins) and expiratory (Vexp) volumes of a patient 102. As a non-limitative example, the sensor 101 may comprise a pneumotachograph or any other suitable sensor. The sensor 101 is connected to the patient's airways to detect the inspiratory (Vins) and expiratory (Vexp) volumes.

A calculator 103 is responsive to the inspiratory (Vins) and expiratory (Vexp) volumes detected by the sensor 101 to calculate a difference between the detected inspiratory (Vins) and expiratory (Vexp) volumes of the patient.

An indicator 104 is responsive to the difference between the detected inspiratory (Vins) and expiratory (Vexp) volumes of the patient, for example the ratio Vins/Vexp, to indicate dynamic hyperinflation.

A controller 105 is connected to the sensor 101, the calculator 103 and a mechanical ventilator 106 providing mechanical ventilation to the patient 102.

A method 200 (FIG. 2) for determining dynamic hyperinflation during mechanical ventilation of a spontaneously breathing patient using the device of FIG. 1 will now be described with reference both to FIGS. 1 and 2.

Figure 2:
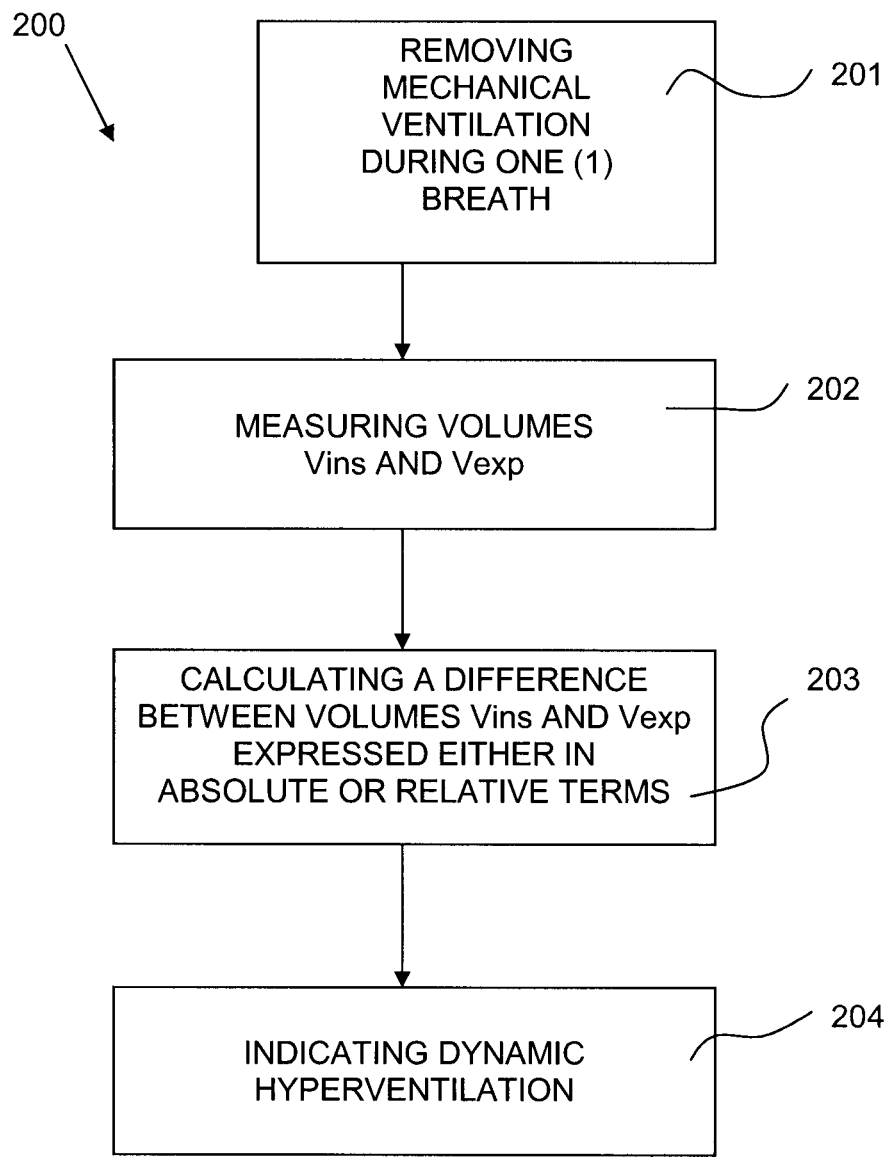
FIG. 2 is a flow chart of a method for determining dynamic hyperinflation during mechanical ventilation of a patient.

Operation 201 (FIG. 2)

The controller 105 (FIG. 1) controls the mechanical ventilator 106 (FIG. 1) to remove mechanical ventilation of the patient 102 (FIG. 1) during one (1) breath of the patient 102 (FIG. 1).

Operation 202 (FIG. 2)

The controller 105 (FIG. 1) controls the sensor 101 (FIG. 1), for example a pneumotachograph, to measure:

the volume (Inspiratory volume Vins) inhaled by the patient 102 (FIG. 1) during the one (1) breath during which mechanical ventilation of the patient 102 (FIG. 1) by the mechanical ventilator 106 (FIG. 1) is removed; and the volume (Expiratory volume Vexp) exhaled by the patient 102 (FIG. 1) during the one (1) breath during which mechanical ventilation of the patient 102 (FIG. 1) by the mechanical ventilator 106 (FIG. 1) is removed.

For that purpose, the sensor 101 (FIG. 1) is connected to the airways of the patient 102 (FIG. 1).

Operation 203 (FIG. 2)

The controller 105 (FIG. 1) also commands the calculator 103 (FIG. 1) to calculate a difference between the inspiratory volume (Vins) and the expiratory volume (Vexp) as measured by the sensor 101 (FIG. 1) during the one (1) breath during which mechanical ventilation of the patient 102 (FIG. 1) by the mechanical ventilator 106 (FIG. 1) is removed. The calculated difference can be expressed either in absolute (for example a mathematical difference between Vins and Vexp) or relative (for example a ratio between Vins and Vexp) terms.

More specifically, for the one (1) breath without mechanical ventilation from the mechanical ventilator 106 (FIG. 1), the calculator 103 calculates the difference between the inspiratory volume (Vins) and the expiratory volume (Vexp) as measured by the sensor 101 (FIG. 1), for example a ratio (Vins/Vexp) between these inspiratory (Vins) and expiratory (Vexp) volumes as measured by the sensor 101 during the one (1) breath during which mechanical ventilation of the patient 102 (FIG. 1) by the mechanical ventilator 106 (FIG. 1) is removed.

If the ratio (Vins/Vexp) is close to 1 this suggests that the patient 102 is able to exhale the same amount of air as was inhaled during the one (1) breath without mechanical ventilation, suggesting that air-trapping due to the mechanical ventilator 106 (FIG. 1) does not have a major impact and that dynamic hyperinflation induced by mechanical ventilation is not present.

However, if the ratio (Vins/Vexp) becomes close to 0, this indicates that the patient 102 (FIG. 1) has considerable problems related to inspiration relative to expiration and that the mechanical ventilator 102 (FIG. 1) induces air-trapping in the lungs of the patient 102 (FIG. 1) and therefore dynamic hyperinflation.

Operation 204 (FIG. 2)

An indicator 104 (FIG. 1) is responsive to the ratio (Vins/Vexp) from the calculator 103 (FIG. 1) to indicate dynamic hyperinflation of the patient.

For example, the indicator 104 (FIG. 1) may produce a light signal going from e.g. green if the ratio (Vins/Vexp) is close to 1 to indicate that dynamic hyperinflation is not present and change towards e.g. red if the ratio (Vins/Vexp) is close to 0 to indicate that dynamic hyperinflation is present.

Also, the ratio (Vins/Vexp) could be used to guide conventional titration of external PEEP, or in combination with previous neural PEEP titration methods (US Published Patent Applications 2005/0211246 and 2003/0226565).

Figure 3:
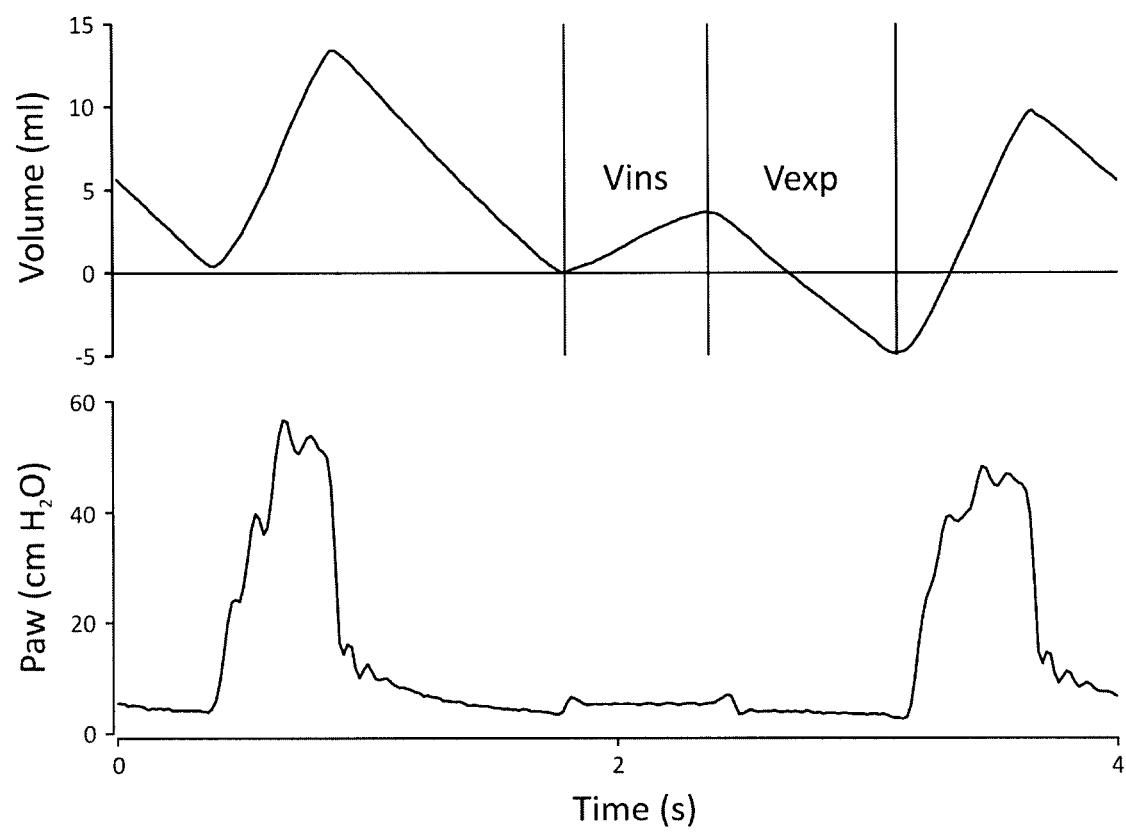
FIG. 3 are graphs showing volume and airway pressure (Paw) over time during breaths of a mechanically ventilated patient and during breaths of a non-mechanically ventilated patient.

FIG. 3 represents graphs showing volume and airway pressure (Paw) over time during breaths with mechanical ventilation and breaths without mechanical ventilation. An example of segments where inspiratory (Vins) and expiratory (Vexp) volumes are measured during the one (1) breath during which mechanical ventilation of the patient 102 (FIG. 1) by the mechanical ventilator 106 (FIG. 1) is removed, are indicated by vertical lines. As shown by the bottom curve of FIG. 3, the mechanical ventilator 106 is controlled by the controller 105 to maintain a level of positive pressure (PEEP) in the patient's airways during the one (1) breath during which mechanical ventilation from the mechanical ventilator 106 is removed.

Figure 4:
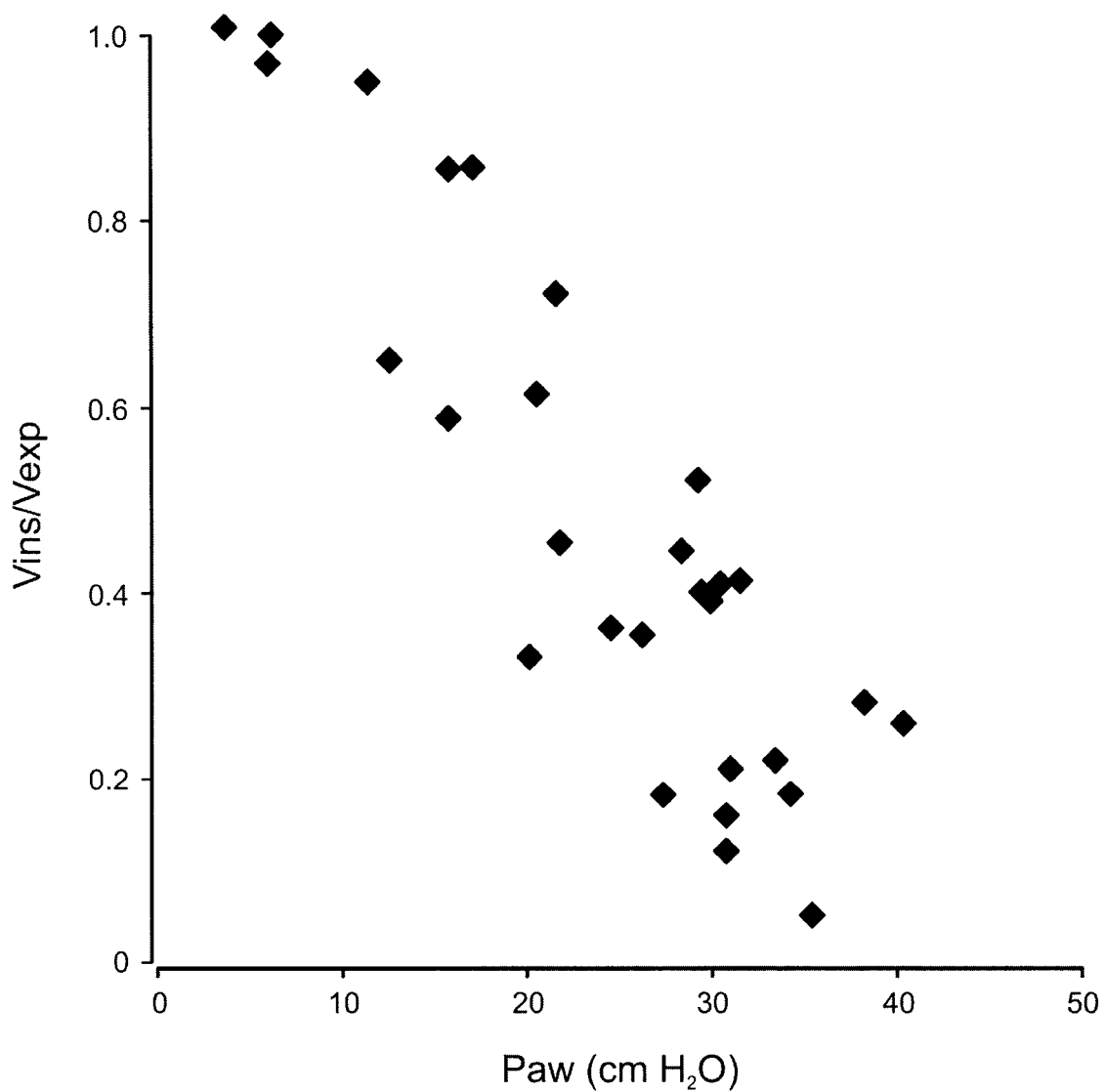
FIG. 4 is a graph showing how the ratio Inspiratory Volume (Vins)/Expiratory Volume (Vexp) of a patient decreases during increasing levels of mechanical ventilation (airway pressure Paw) when breathing against a high inspiratory and expiratory resistive load.

In the graph of FIG. 4, the points show how the ratio (Vins/Vexp) decreases with increasing levels of mechanical ventilation of the patient 102 (FIG. 1) by the mechanical ventilator 106 (FIG. 1) when the patient 102 breathes against a high inspiratory and expiratory resistive load.

Figure 5:
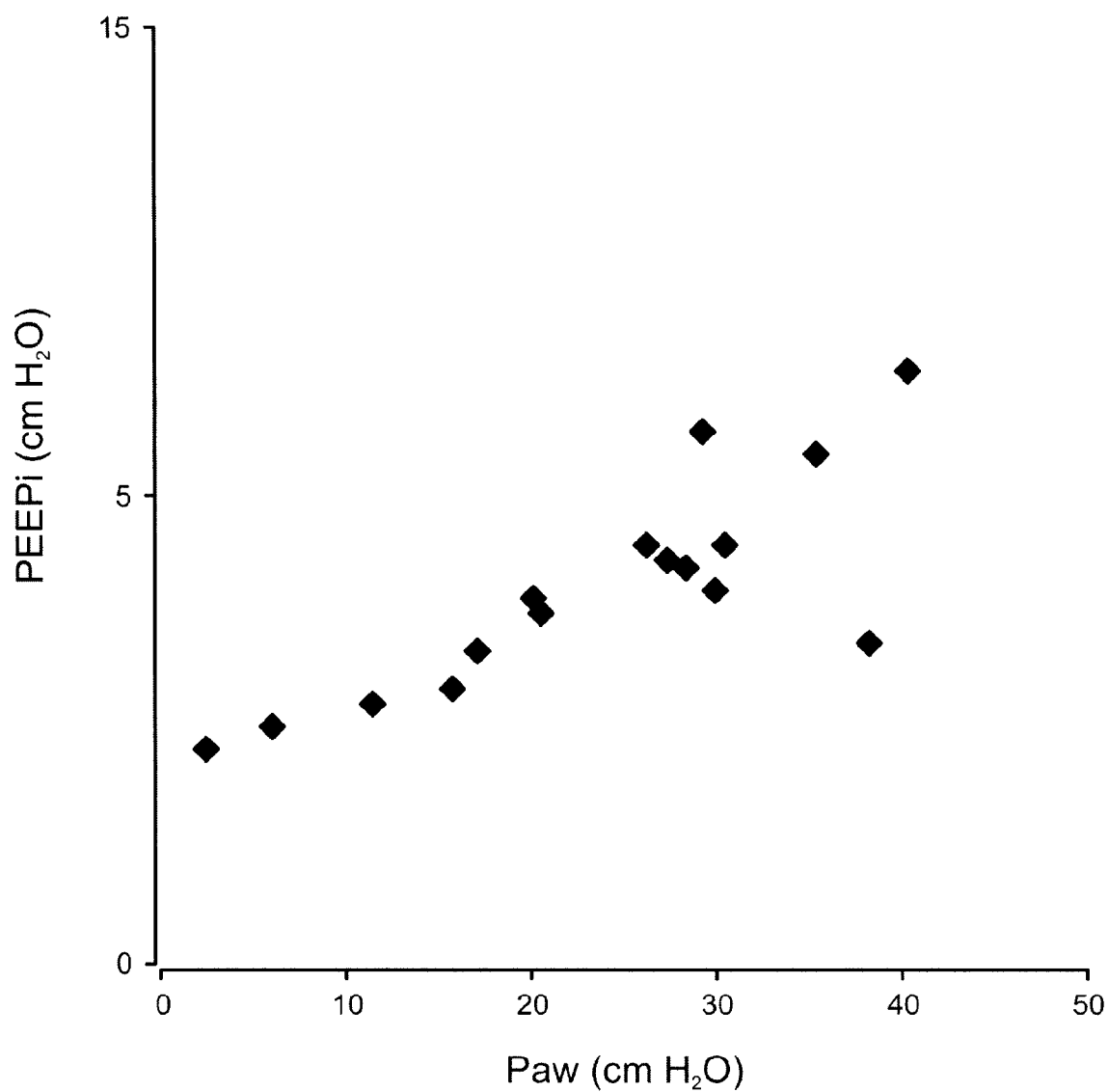
FIG. 5 is a graph showing how values of intrinsic PEEP or PEEPi increases during increasing levels of mechanical ventilation (airway pressure Paw) when the patient breathes against a high inspiratory and expiratory resistive load; the graph of FIG. 5 results from the same recordings as the graph of FIG. 4.

In the graph of FIG. 5, the points show how conventional PEEPi values increase with increasing levels of mechanical ventilation of the patient 102 (FIG. 1) by the mechanical ventilator 106 (FIG. 1) when the patient 102 breathes against a high inspiratory and expiratory resistive load (same recordings as in FIG. 4).

The sensor 101 (FIG. 1), for example a pneumotachograph, may measure during operation 202 the inspiratory volume (Vins) and the expiratory volume (Vexp) during a plurality of successive or non successive singles breaths during which mechanical ventilation of the patient 102 (FIG. 1) by the mechanical ventilator 106 (FIG. 1) is removed. The calculator 103 (FIG. 1) then compute the ratio (Vins/Vexp) for example as an average of the ratios (Vins/Vexp) calculated from the inspiratory (Vins) and expiratory (Vexp) volumes measured by the sensor 101 during the respective single breaths without mechanical ventilation.

Also, the above described method 200 (FIG. 2) for determining dynamic hyperinflation during mechanical ventilation of a spontaneously breathing patient can be implemented at any given level of mechanical ventilation delivered by the mechanical ventilator 106 (FIG. 1) in any type of mechanical ventilation mode.

What is claimed is:

1. A method for determining dynamic hyperinflation during mechanical ventilation of a spontaneously breathing patient, comprising:

removing, using a controller, mechanical ventilation during one breath of the patient;

measuring inspiratory and expiratory volumes of the patient during said one breath;

calculating, using a calculator, a difference between the inspiratory and expiratory volumes measured during said one breath, the calculated difference having a value; and indicating, using an indicator, presence or absence of dynamic hyperinflation of the patient's lungs on the basis of a position of the value of the calculated difference with respect to a first value indicative of presence of dynamic hyperinflation and a second value indicative of absence of dynamic hyperinflation.

2. A method for determining dynamic hyperinflation as defined in claim 1, wherein measuring the inspiratory volume comprises measuring a volume inhaled by the patient during said one breath during which mechanical ventilation is removed.

3. A method for determining dynamic hyperinflation as defined in claim 1, wherein measuring the expiratory volume comprises measuring a volume exhaled by the patient during said one breath during which mechanical ventilation is removed.

4. A method for determining dynamic hyperinflation as defined in claim 1, wherein calculating the difference comprises calculating a ratio between the inspiratory and expiratory volumes measured during said one breath.

5. A method for determining dynamic hyperinflation as defined in claim 1, wherein calculating the difference comprises calculating a ratio Vins/Vexp between the inspiratory volume Vins and the expiratory volume Vexp measured during said one breath.

6. A method for determining dynamic hyperinflation as defined in claim 5, wherein the first value is 0 and the second value is 1, and wherein indicating dynamic hyperinflation comprises indicating that dynamic hyperinflation is absent when the ratio Vins/Vexp is close to 1 and indicating that dynamic hyperinflation is present when the ratio Vins/Vexp is close to 0.

7. A method for determining dynamic hyperinflation as defined in claim 1, wherein said one breath comprise a plurality of successive or non successive single breaths during which mechanical ventilation of the patient is removed.

8. A method for determining dynamic hyperinflation as defined in claim 7, wherein measuring the inspiratory and expiratory volumes comprise measuring the inspiratory and expiratory volumes during said plurality of single breaths, and wherein calculating the difference comprises calculating a ratio Vins/Vexp from the inspiratory volumes Vins and the expiratory volumes Vexp measured during said plurality of single breaths.

9. A method for determining dynamic hyperinflation as defined in claim 1, wherein removing mechanical ventilation during one breath of the patient comprises maintaining a level of positive pressure in the patient's airways during said one breath.

10. A device for determining dynamic hyperinflation during mechanical ventilation of a spontaneously breathing patient, comprising:
   a controller for removing mechanical ventilation during one breath of the patient;
   a sensor of inspiratory and expiratory volumes of the patient during said one breath;
   a calculator of a difference between the inspiratory and expiratory volumes sensed during said one breath, the calculated difference having a value; and
   an indicator of presence or absence of dynamic hyperinflation of the patient's lungs on the basis of a position of the value of the calculated difference with respect to a first value indicative of presence of dynamic hyperinflation and a second value indicative of absence of dynamic hyperinflation.

11. A device for determining dynamic hyperinflation as defined in claim 10, wherein the sensor is adapted to be connected to patient's airways to measure as the inspiratory volume a volume inhaled by the patient during said one breath during which mechanical ventilation is removed.

12. A device for determining dynamic hyperinflation as defined in claim 10, wherein the sensor is adapted to be connected to patient's airways to measure as the expiratory volume a volume exhaled by the patient during said one breath during which mechanical ventilation is removed.

13. A device for determining dynamic hyperinflation as defined in claim 10, wherein the calculator of the difference calculates a ratio between the inspiratory and expiratory volumes measured during said one breath.

14. A device for determining dynamic hyperinflation as defined in claim 10, wherein the calculator of the difference calculates a ratio Vins/Vexp between the inspiratory volume Vins and the expiratory volume Vexp measured during said one breath.

15. A device for determining dynamic hyperinflation as defined in claim 14, wherein the first value is 0 and the second value is 1, and wherein the indicator indicates that dynamic hyperinflation is absent when the ratio Vins/Vexp is close to 1 and indicates that dynamic hyperinflation is present when the ratio Vins/Vexp is close to 0.

16. A device for determining dynamic hyperinflation as defined in claim 10, Wherein said one breath comprise a plurality of successive or non successive single breaths during which mechanical ventilation of the patient is removed.

17. A device for determining dynamic hyperinflation as defined in claim 16, wherein the sensor measures the inspiratory and expiratory volumes during said plurality of single breaths, and wherein the calculator of the difference calculates a ratio Vins/Vexp from the inspiratory volumes Vins and the expiratory volumes Vexp measured during the plurality of single breaths.

18. A device for determining dynamic hyperinflation as defined in claim 10, wherein the controller is connected to:
   a mechanical ventilator providing mechanical ventilation of the patient to control the mechanical ventilator to remove the mechanical ventilation during said one breath;
   the sensor of inspiratory and expiratory volumes to control said sensor to measure the inspiratory and expiratory volumes during said one breath; and
   the calculator of the difference to control said calculator to calculate the difference between the inspiratory and expiratory volumes measured during said one breath.

19. A device for determining dynamic hyperinflation as defined in claim 10, wherein the controller controls the removal of mechanical ventilation during said one breath of the patient to maintain a level of positive pressure in the patient's airways during said one breath.

* * * * *